United States Patent [19]

Gerhart

[11] 4,121,467
[45] Oct. 24, 1978

[54] NON-DESTRUCTIVE TECHNIQUE FOR SURFACE WAVE VELOCITY MEASUREMENT

[75] Inventor: Grant R. Gerhart, Bloomfield Hills, Mich.

[73] Assignee: The United States of America as represented by the Secretary of the Army, Washington, D.C.

[21] Appl. No.: 801,508

[22] Filed: May 31, 1977

[51] Int. Cl.² .............................................. G01N 29/00
[52] U.S. Cl. ......................................... 73/597; 73/629
[58] Field of Search .............. 73/67.8 R, 67.7, 67.5 R, 73/560, 67.9, 597, 620, 629, 645, 646; 333/30 R

[56] References Cited

U.S. PATENT DOCUMENTS

| 3,812,709 | 5/1974 | Benson et al. | 73/67.8 R |
| 3,946,256 | 3/1976 | Day et al. | 73/67.5 R |
| 4,013,983 | 3/1977 | Hartemann | 333/30 R |
| 4,028,648 | 6/1977 | Hartmann et al. | 333/30 R |

OTHER PUBLICATIONS

Papadakis, "New Compact Instrument for Pulse-Echo-Overlap Measurement of Ultrasonic Wave Transit Times", Review of Scientific Instruments, 7-1976, pp. 806-813.
Hellier et al., "Pulse Echo Overlap for Measurement of Velocity of Sound", Journal of Physics E, pp. 352-354, 5-1975.
Sagnes et al., "Oscilloscope for Velocity Measurements of Acoustic Surface Waves," Electronics Letter, pp. 421-422, 8-1972.
Cook et al., "Surface Waves at Ultrasonic Frequencies," ASTM Bulletin, pp. 81-84, 5-1954.

*Primary Examiner*—Stephen A. Kreitman
*Attorney, Agent, or Firm*—Peter A. Taucher; John F. Schmidt; Nathan Edelberg

[57] ABSTRACT

It is often desirable to measure absolute and relative USW velocities in a specimen. One example is a specimen which is to be tested for residual surface stresses. The specimen is provided with two scratches which are parallel and a known distance apart. An ultrasonic surface wave (USW) transducer is attached to the surface of the specimen in such a way as to efficiently transfer USW energy to the specimen. During testing, the incident pulse from the transducer is partially reflected at each scratch. The same transducer generates and detects both reflections. The transducer output goes through a clipping circuit which clips the large incident voltage spikes in the output and passes the smaller, echo voltages through to an oscilloscope. The oscilloscope horizontal sweep is driven at a frequency which is the reciprocal of the difference in arrival times between the two reflected pulses.

A dual pulse delay generator is detailed as a double strobe delay generator having a plurality (herein six) of integrated circuits (IC's) interconnected as described below to provide the Z-axis input to the oscilloscope.

8 Claims, 4 Drawing Figures

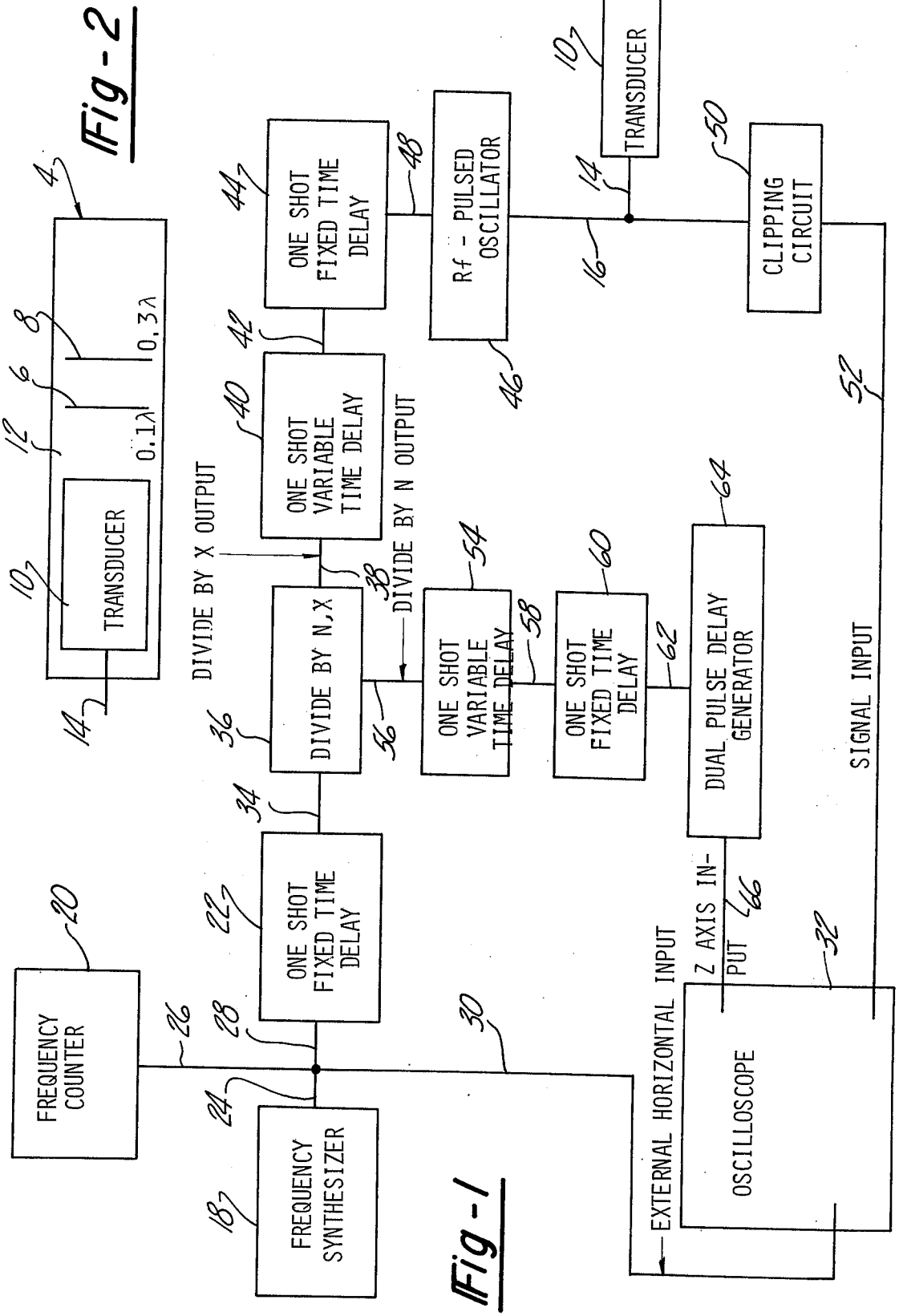

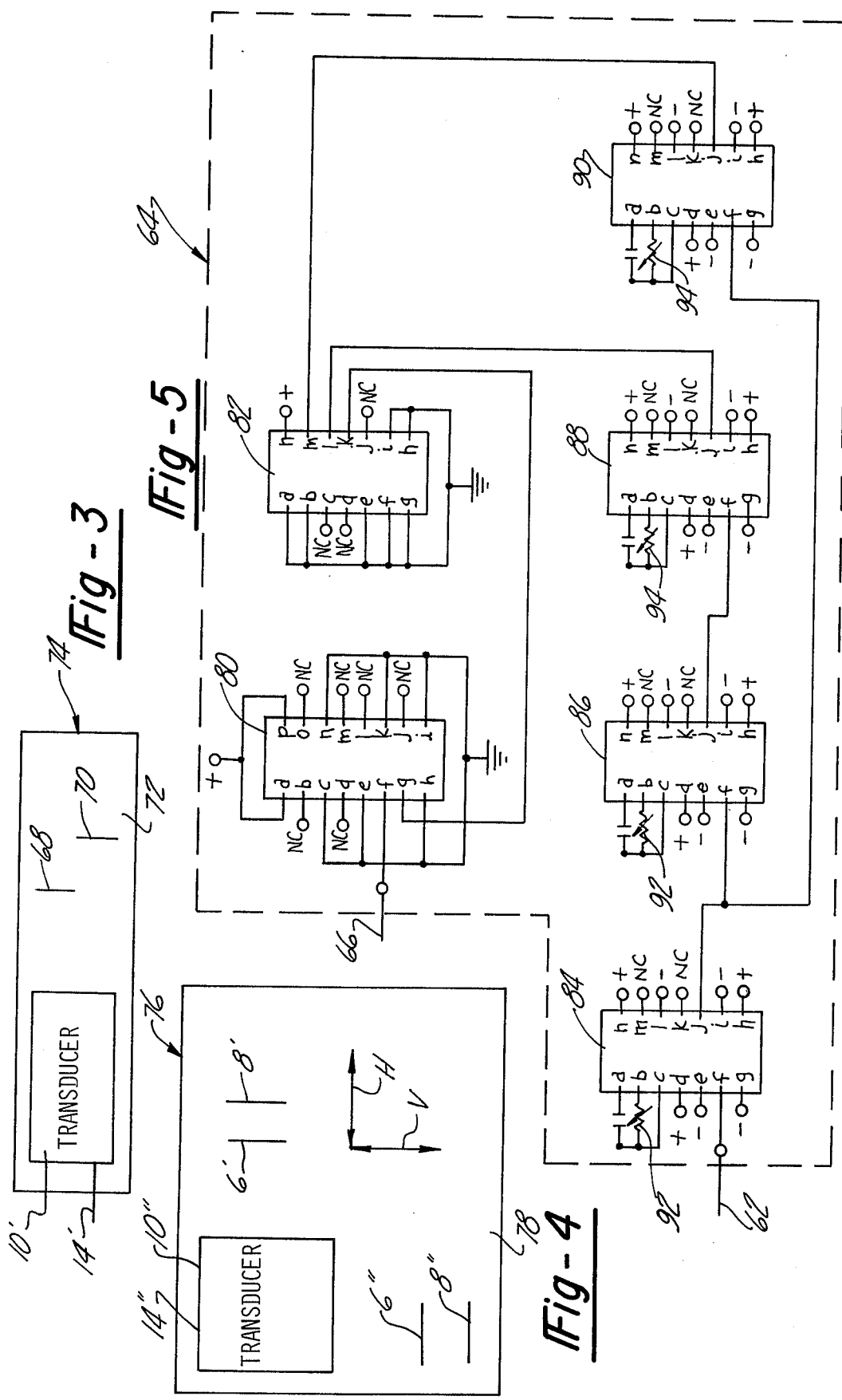

NON-DESTRUCTIVE TECHNIQUE FOR SURFACE WAVE VELOCITY MEASUREMENT

The invention described herein may be manufactured, used, and licensed by or for the Government for governmental purposes without payment to me of any royalty thereon.

BACKGROUND OF THE INVENTION

1. Field of the Invention

The invention is a new technique for measuring the velocity of ultrasonic surface waves (USW) propagated on the surface of a test specimen which has been provided with two parallel scratches spaced apart a precisely known distance, for the purpose of measuring the elastic mechanical parameters of the specimen near its surface by applying an external static stress (which may be zero or non-zero) on that surface, in order to determine the residual stress and the mechanical strength properties of the specimen.

2. Description of the Prior Art

Inasmuch as the accuracy of the USW absolute velocity measurements depends upon a precisely known distance traversed in a precisely measured time interval between generation and detection of the USW signal, it follows that an imprecise determination of said distance, and coupling variations between the transducer and the specimen surface will greatly limit the accuracy of the USW velocity measurements.

Prior Art methods for measuring USW velocity are extremely accurate for making relative measurements when the propagation distance and the applied external stress state are constant but not necessarily known. On the other hand, an absolute velocity measurement requires precise knowledge of the propagation distance, and constant coupling conditions. A major problem in prior art methods is the difficulty which those two limitations impose upon the accurate measurement of absolute USW velocity measurements. Consequently, it is extremely difficult to measure accurately either the second or third order elastic constants of the specimen.

Moreover, the coupling variations become completely unmanageable when the USW velocity measurements are made in the presence of an externally applied stress that causes a relative strain or deformation of the coupling agent at the interface between the specimen and the transducer. Another problem is the difficulty of precisely determining the actual propagation distance between the two transducers, because a transducer is not a point source and the exact origin of the USW in the transducer is difficult to determine accurately.

Another prior art method is described in: *Elements of X-Ray Diffraction*, by B. D. Cullity, copyright 1956, chapter 17, "Stress Measurement", published by Addison-Wesley Publishing Co., Inc.; SAE undated Pub. No. TR-182, "Measurement of Stress by X-Ray", by Christensen, ed, Koistinen and Marburger, GMC, Semchysen, Climax Moly, and W. P. Evans, Caterpillar; and GM Res. Labs. Pub. GMR-825, "GMR Fas-Tress: A Fast Automatic Stress Analyser," 1968.

SUMMARY OF THE INVENTION

One advantage of this invention is that the transducer which generates the USW radiation is also the transducer which detects the reflected wave. The detected signals are two reflected echoes which bounce off two parallel, spaced scratches on the surface of the specimen being tested. The spacing, contour, and orientation of the scratches are precisely controlled by a computer-guided, pulse laser system. The depth of the scratches can be tailored so that the reflected echoes are approximately equal in magnitude.

Distortions which might originate in coupling variations between the transducer and the specimen affect the two echoes equally. Consequently, the relative position of the two signals is unchanged in time on the oscilloscope.

Accordingly, an object of the invention is to measure the USW velocity in a test specimen by dividing twice the scratch separation distance by the difference in transit times of the two reflected echoes. Each of these two quantities is measured accurately and independently of the other. The relative transit time difference is measured by the pulse overlap method. These measurements will give both the absolute and relative velocities of the USWs propagated on a test specimen surface independent of external stress configurations.

IN THE DRAWINGS

FIG. 1 is a circuit block diagram providing a schematic drawing of the components and their electrical interconnection.

FIG. 2 is a schematic drawing of a test specimen provided with one arrangement of parallel scratches, and showing a transducer mounted on one of its surfaces.

FIG. 3 is a schematic drawing similar to FIG. 2 but showing an alternative arrangement of parallel scratches.

FIG. 4 shows a transducer on a test specimen provided with two sets of parallel scratches, one set being arranged at right angles to the other; and FIG. 5 is a detailed schematic drawing showing a circuit block diagram of one of the components shown in FIG. 1.

DESCRIPTION OF A PREFERRED EMBODIMENT

In the embodiment shown in FIG. 2, a test specimen 4 is provided with two parallel scratches 6 and 8, a known distance apart and a few thousandths of an inch deep. Thus, scratch 6 has a depth that is approximately 10% of the wavelength of the propated USW, and the depth of scratch 8 is approximately 30% of that wavelength — i.e., about three times as deep as scratch 6.

A high power pulsed laser such as a YAG or a $CO_2$ laser, can be computer-controlled with focusing optics to rapidly inscribe scratches 6 and 8 to a high degree of accuracy for depth, width, contour and distance between scratches. A USW transducer 10 is attached to surface 12 in any suitable conventional manner.

Transducer 10 is connected by a conductor 14 with a conductor 16 so that the transducer output signal can be fed into the instrumentation circuitry.

Passing now to the other side of the loop of the FIG. 1 circuit diagram, a frequency synthesizer 18 and a frequency counter 20 are connected to a mono-stable multi-vibrator one-shot fixed time delay 22 by means of conductors 24, 26 and 28, which conductors connect with a conductor 30 to provide the external horizontal input to an oscilloscope 32.

The fixed time delay 22 delivers its signal via a conductor 34 to a programmable divide by N, X counter 36. The counter's X output (X varies from 2 to N) goes via a conductor 38 to a one-shot variable time delay 40, of which the output signal is delivered via a conductor 42 to a one-shot technique time delay 44. An Rf pulsed oscillator 46 receives the output signal of fixed time delay 44 via a conductor 48. Pulsed oscillator 46 is connected with conductor 16, by which oscillator 46 and transducer 10 are connected to a clipping circuit 50, which transmits a clipped signal from transducer 10 to oscilloscope 32 via a conductor 52.

Returning now to the divide by N, X 36, the divide by N output goes to a one-shot variable time delay 54 via a conduit 56. From variable time delay 54, the signal is transmitted via a conductor 58 to a one-shot fixed time delay 60.

Fixed time delay 60 outputs via a conductor 62 to a dual pulse delay generator 64, which provides, via a conductor 66, the Z-axis input to oscilloscope 32.

THE EMBODIMENT OF FIG. 3

FIG. 3 shows a scratch pattern which offers an alternative to the pattern shown in FIG. 2. In FIG. 3, two parallel scratches 68 and 70 of substantially identical depth are provided in the surface 72 of a test specimen 74. The two scratches are offset in the direction of the scratches so that part of the USW propagated by transducer 10' bypasses scratch 68 and is reflected by scratch 70.

THE EMBODIMENT OF FIG. 4

In FIG. 4, another adaptation of the invention is illustrated. A test specimen 76 is there shown having a pair of parallel scratches 6' and 8' inscribed in surface 78, similar to the scratches 6 and 8 of the FIG. 1 embodiment, disposed to reflect USW propagated by transducer 10" in a direction indicated by arrow H. A second pair of parallel scratches 6" and 8" is shown inscribed in surface 78, also similar to the scratches 6 and 8 of the FIG. 1 embodiment, disposed to reflect USWs propagated by transducer 10" in a direction indicated by arrow V. Arrows H and V are at right angles to each other. Such an application of the invention is useful in determining whether the test specimen 76 is isotropic or anisotropic, as will be detailed below in a discussion of the operation of the illustrated embodiments.

THE GATING CIRCUIT, FIG. 5

The dual pulse delay generator shown at 64 in FIG. 1 can conceivably be one of a number of devices. A preferred embodiment of such a dual pulse delay generator is detailed in FIG. 5.

As will be understood by those skilled in the art, the device 64 serves as a gating circuit. As such, it is capable of: providing a voltage which pulses the Z-axis intensity modulation control or selectively triggers a transistor circuit which gates directly the input signal to the oscilloscope synchronously with the arrival of the two reflected echoes from the parallel scratches.

As shown in FIG. 5, dual pulse delay generator 64 comprises six interconnected commercially available (from RCA or Texas Instruments, for example) integrated circuits (ICs), 80, 82, 84, 86, 88 and 90. The four ICs 84, 86, 88 and 90 are identical, and can conveniently be standard catalog No. CD 4047 of RCA, while IC 80 is catalog No. CD 4009 and IC 82 is No. CD 4001.

Each capacitor shown in FIG. 5 has a capacitance of 0.0047 microfarad. The pins $b$ of ICs 84 and 86 are connected to variable resistors 92, each of which has a resistance of 50,000 ohms in series with a 470 ohm resistor. Each of ICs 88 and 90 has a pin $b$ connected with a variable resistor 94 of 10,000 ohms in series with a 220 ohm resistor.

The pins in FIG. 5 marked "NC" have no connection. Pins which are connected with a negative power source and others connected with a positive power source are conventionally labelled − and + respectively, as shown. Pins $c$, $e$, $h$, $i$, $k$, and $n$ of IC 80, and pins $a$, $b$, $e$, $f$, $g$, $h$, and $i$ of IC 82 are grounded, as shown.

OPERATION

The transducer 10 (or 10', or 10") generates an incident USW which propagates toward the scratches and is reflected back toward the transducer. Scratch dimensions are small compared to the USW wavelength so that multiple reflections are negligible and the incident USW amplitude is only slightly diminished by the presence of the scratch nearer to the transducer. The relative sizes of the two scratch geometries is tailored so that the two reflected echoes are roughly equal. A computer-controlled YAG laser such as the Korad Model KSS314 has been successfully used to precisely scribe the pair of parallel scratches on the surface.

The incident pulse from the transducer 10 is partially reflected at each of the two scratches and is detected by the same transducer. This has the advantage of eliminating relative coupling variations which would introduce errors by the use of one transducer to generate the USW and a different transducer to detect the echo. The transducer output goes directly, via conductors 14 and 16, to clipping circuit 50 which clips the large incident voltage spikes, but passes the echo voltages to oscilloscope 32, of which the horizontal sweep is driven externally at a frequency which is the reciprocal of the difference in arrival times between the two reflected pulses (or echoes).

When the frequency is adjusted to a proper value, the two pulse traces are superimposed on the oscilloscope screen. The surface wave velocity $v$ is $$v = 2df$$

wherein $d$ is the separation distance between scratches, and $f$ is the frequency of the voltage which drives the horizontal sweep.

Applied stresses change the coupling between the specimen and the transducer, with the result that the arrival times of the two reflected pulses (echoes) vary substantially. However, the variations in arrival times for both pulses are the same, with the consequence that the relative time difference remains the same (i.e., is a constant). Thus, the pulse overlap techniques measures the relative time difference and so is able to determine SW velocity values which are independent of coupling errors.

Returning to frequency synthesizer 18, the output signal triggers the circuit of one-shot fixed time delay device 22, of which the output is a narrow (2µ sec) pulse which triggers the divide counter 36. The outputs of counter 36 divide the input frequency by N and X. As pointed out above, X varies from 2 to N. Both outputs are reset by the divide-by-N output pulse, so that the result is a relative digital delay time interval between the output pulses from counter 36 to each of the one-shot variable time delay devices 40 and 54.

The outputs of devices 40 and 54 have a variable pulse width which is determined by an adjustable RC time constant. The one-shot fixed time delay devices 44 and 60 trigger off the lagging edges of the outputs from variable time delay devices 40 and 54 respectively to provide a continuously adjustable analog delay.

The input to dual pulse delay generator 64 consists of an analog delay and digital delay in series. By itself, the analog delay produces excessive oscilloscope trace jitter for large delay times; it is therefore desirable to keep the analog delay as small as possible.

The circuit of dual pulse delay generator 64 produces two output pulses of variable width and pulse height. One of those pulses is delayed relative to the other, and both are inputted to the Z-axis input of oscilloscope 32. The Z-axis illumination control allows the operator to enhance the two overlapping reflected echoes and eliminate the many spurious reflected echoes. One-shot fixed time delay device 44 triggers the Rf-pulsed oscillator 46 which pulses transducer 10.

Overlapping of the two reflected echoes is accomplished by adjusting the frequency of synthesizer 18 and by positioning the traces by means of the various analog and digital time delays 40, 44, 54 and 60.

OPERATION OF FIG. 3 EMBODIMENT

In FIG. 3, where the scratches are offset in the path of the transducer pulses, the scratches 68 and 70 are the same depth. If the amplitude of the reflected echoes tends to be less than the amplitude of the echoes in the FIG. 2 embodiment, compensation for that can be accomplished by scribing both scratches deeper.

OPERATION OF FIG. 4 EMBODIMENT

In the FIG. 4 embodiment, velocity measurements in the H and V directions will have the same value if the specimen 76 is elastic, isotropic, and homogeneous. If the two values differ, the difference is a function of the anisotropy of the specimen. In many of the applications of metals, this anisotropy is small. It can be, and usually is, the result of preferential working processes, such as rolling, stamping, milling, forging, bending, and the like.

For an isotropic, homogeneous material, the Rayleigh Wave equation gives the USW velocity, V, as a function of the shear and longitudinal wave velocities $V_t$ and $V_l$:

$$\eta^6 - 8\eta^4 + 8(3 - 2\xi^2)\eta^2 - 16(1 - \xi^2) = 0$$

wherein $$\eta = V/V_t$$

$$\xi = V_t/V_l$$

For a reference text, see *Rayleigh and Lamb Waves*, by I. A. Viktorov, Plenum Press 1967.

The sixth-order equation in $\eta$ can be solved numerically; for many purposes, an approximate solution is appropriate as $$V = \frac{(0.87 + 1.12\nu)}{1 + \nu} V_s$$

$$\nu = \frac{V_l^2 - 2V_s^2}{2(V_l^2 - V_s^2)}$$

The Rayleigh Wave velocity V is directly related to the two independent elastic constants for an isotropic material. Another independent velocity measurement is needed to determine the two constants uniquely. Such additional independent measurement could be made on a transverse wave where the displacement vector is parallel to the surface. Only the shear-wave displacement component that is perpendicular to the surface couples with the longitudinal displacement to produce a Rayleigh Wave. Thus it would be possible to effect simultaneous measurement of V and $V_t$ to determine the two elastic constants.

The measurement of V by itself is important because variations in V are related to changes in the elastic constants. Measurement of V can be used as a method of determining the mechanical homogeneity of a number of specimens for quality control purposes. Stated tolerance specifications in V can be used as a guideline for the acceptance or rejection of a part on the basis of its mechanical properties - strength, for example.

The average residual stress concentration between the scratches can be related to the RW velocity through the use of an appropriate RW equation for small anisotropic effects which are produced by residual stresses.

$$\frac{\Delta V}{V_0} = J\frac{C^1_{33}}{C^0_{33}} + K\frac{C^1_{31}}{C^0_{33}} + L\frac{C^1_{53}}{C^0_{55}} +$$

$$(M + 0.5)\frac{C^1_{55}}{C^0_{55}} + N\frac{C^1_{11}}{C^0_{11}} - 0.5 \Delta\rho/\rho^0$$

$$C^1_{ij} = C_{ijk}S_k$$

where $C_{ijk}$ is a component of the third order elastic constant tensor, $S_k$ is the $K_{th}$ component of the abbreviated strain tensor and J, K, L, etc are calculated from the measured values of the second-order elastic constants. For a reference text, see my paper *Rayleigh Wave Velocity for a Stress-Induced Slightly Anisotropic Solid*, J. Acoust. Soc. Am., Vol. 60, No. 5. Nov. 1976, pp. 1085 - 1088. For the case of 5086H32 aluminum plate, the above equation for ($\Delta V/V°$) simplifies to $$\frac{\Delta V}{V^0} = -6.39 \times 10^{-10} T$$

where T is the magnitude of a uniaxial stress component which is parallel to the propagation direction of the RW. A compression or tension residual stress is a uniaxial stress configuration and its average value in the depth of propagation of the RW is related to ($\Delta V/V°$) through the above-identified simplified equation. It is further noted that a tensile stress produces a negative change in $\Delta V$ and a compressive stress produces a positive change in $\Delta V$.

I wish it to be understood that I do not desire to be limited to the exact details of construction shown and described for obvious modifications will occur to a person skilled in the art.

I claim:

1. A device for measuring absolute and relative USW velocities in a specimen comprising:

a. a specimen sample having a surface with two parallel scratches spaced a precise known distance apart;

b. one only ultrasonic surface wave transducer adapted to be coupled to the scratched surface of the specimen for propagating a succession of pulsed surface waves along the scratched surface across the scratches, whereby the coupling errors between said one only transducer and the scratched surface are substantially the same for the echoes from both of the two scratches;

c. an oscilloscope having a horizontal sweep circuit, and a vertical sweep circuit;

d. means to drive the horizontal sweep circuit at a frequency which is the reciprocal of the difference in arrival times between pulses reflected from the two scratches; and e. means to transmit the reflected pulse voltages of the transducer to the vertical sweep circuit.

2. A device as in claim 1, and means to eliminate spurious signals to the oscilloscope.

3. A device as in claim 2, wherein the means to eliminate spurious signals comprises a dual pulse delay circuit to modulate the oscilloscope trace to enhance the trace image of the two reflected pulses.

4. A device as in claim 3, and means, including an analog delay and a digital delay in series, to generate an input signal to the dual pulse delay circuit.

5. A device to determine the isotropy of a specimen comprising:

a. a specimen sample having a surface provided with a first set of two parallel scratches, and a second set of two parallel scratches perpendicular to the first set, the two scratches of each set spaced a precise known distance apart;

b. one only ultrasonic surface wave transducer adapted to be coupled to the scratched surface of the specimen for propagating a succession of surface waves along the scratched surface and across both sets of parallel scratches, whereby the coupling errors between said one only transducer and the scratched surface are substantially the same for the echoes from both of the two scratches of each set;

c. an oscilloscope having a horizontal sweep circuit, and a vertical sweep circuit;

d. means to drive the horizontal sweep circuit at a frequency which is the reciprocal of the difference in arrival times between pulses reflected from the two scratches of a set of scratches, and e. means to transmit the reflected pulse voltages of the transducer to the vertical sweep circuit.

6. A device as in claim 5, and means to eliminate spurious signals to the oscilloscope.

7. A device as in claim 6, wherein the means to eliminate spurious signals comprises a dual pulse delay circuit to modulate the oscilloscope trace to enhance the trace image of the two pulses reflected from the two scratches of a selected set.

8. A device as in claim 7, and means, including an analog delay and a digital delay in series, to generate an input signal to the dual pulse delay circuit.

* * * * *